United States Patent [19]
Davis et al.

[11] Patent Number: 5,192,535
[45] Date of Patent: Mar. 9, 1993

[54] OPHTHALMIC SUSPENSIONS

[75] Inventors: Jeffrey P. Davis, Madison, Wis.; Santosh K. Chandrasekaran, Moraga, Calif.; Yansheng Su, Shandong, China; Roy D. Archibald, Fremont, Calif.; Joseph R. Robinson, Madison, Wis.

[73] Assignee: InSite Vision Incorporated, Alameda, Calif.

[21] Appl. No.: 544,518

[22] Filed: Jun. 27, 1990

Related U.S. Application Data

[63] Continuation-in-part of Ser. No. 537,005, Jun. 12, 1990, abandoned, which is a continuation of Ser. No. 301,114, Jan. 25, 1989, abandoned, which is a continuation-in-part of Ser. No. 153,762, Feb. 8, 1988, abandoned.

[51] Int. Cl.$^5$ .................. A61F 2/14; A61K 9/64; A61K 9/70; A61K 31/765
[52] U.S. Cl. .................. 424/78.04; 424/427; 424/428; 424/443; 424/484; 424/486; 424/487; 514/772.3; 514/772.4; 514/772.6; 514/912; 514/913; 514/914; 514/915; 514/944; 514/953; 514/954
[58] Field of Search .............. 424/78, 427, 428, 443, 424/456, 484, 486, 487, 78.04; 514/724, 912, 913, 914, 915, 944, 953, 954, 772.3–772.04, 772.6; 526/317.1, 318, 318.3, 318.5, 319

[56] References Cited

U.S. PATENT DOCUMENTS

| | | | |
|---|---|---|---|
| 3,947,573 | 3/1976 | Rankin | 424/78 |
| 4,271,143 | 10/1986 | Schoenwald et al. | 424/81 |
| 4,407,792 | 6/1981 | Schoenwald et al. | 424/78 |
| 4,474,751 | 10/1984 | Haslam et al. | 424/14 |
| 4,478,818 | 10/1984 | Shell et al. | 424/80 |
| 4,615,697 | 10/1984 | Robinson | 424/78 |
| 4,820,737 | 4/1989 | Schoenwald et al. | 514/654 |
| 4,911,920 | 3/1990 | Jani et al. | 424/78 |

FOREIGN PATENT DOCUMENTS

| | | |
|---|---|---|
| 2012634 | 2/1990 | Spain . |
| 2007091A | 5/1979 | United Kingdom . |
| 2013084 | 8/1979 | United Kingdom . |
| WO84/04680 | 12/1984 | World Int. Prop. O. . |
| WO84/04681 | 12/1984 | World Int. Prop. O. . |
| WO89/06964 | 8/1989 | World Int. Prop. O. . |

OTHER PUBLICATIONS

Pharmaceutica Acta Helvetiae, vol. 39, pp. 546 et seq. (1964).
Canadian Journal of Pharmaceutical Science, vol. 10, No. 1, pp. 16 et seq. (1975).
Pharmaceutica Acta Helvetiae, vol. 39, pp. 615 et seq. (1964).
Ophthalmology, "Gel Tears", Oct. 1984, vol. 91, No. 10, pp. 1199–1204, Liebowitz et al.
Klin Mbl. Augenheilk, 189, (1986), at pp. 51–54 and pp. 254–257, Marquardt.

Primary Examiner—Thurman K. Page
Assistant Examiner—Carlos Azpuru
Attorney, Agent, or Firm—Freed, Kjeldgaard, Griffin & Inskeep

[57] ABSTRACT

Lightly crosslinked polymers, preferably ones prepared by suspension or emulsion polymerizing at least about 90% by weight of a carboxyl-containing monoethylenically unsaturated monomer such as acrylic acid with from about 0.1% to about 5% by weight of a polyfunctional, and preferably difunctional, crosslinking agent such as divinyl glycol (3,4-dihydroxy-1,5-hexadiene), having a particle size of not more than about 50 μm in equivalent spherical diameter, when formulated with an ophthalmic medicament, e.g., fluorometholone, into suspensions in aqueous medium in which the amount of polymer ranges from about 0.1% to about 6.5% by weight, based on the total weight of the aqueous suspension, the pH is from about 3.0 to about 6.5, and the osmotic pressure (osmolality or tonicity) is from about 10 mOsM to about 400 mOsM, provide new topical ophthalmic medicament delivery systems having suitably low viscosities which permit them to be easily administered to the eye in drop form, and hence be comfortably administrable in consistent, accurate dosages. These suspension will rapidly gel in the eye after coming into contact with the eye's tear fluid to a substantially greater viscosity than that of the originally-introduced suspension and thus remain in place for prolonged periods of time to provide sustained release of the ophthalmic medicament.

35 Claims, No Drawings

OPHTHALMIC SUSPENSIONS

REFERENCE TO RELATED APPLICATION

This application is a continuation-in-part of application Ser. No. 07/537,005, now abandoned, filed on June 12, 1990, which was a file wrapper continuation of application Ser. No. 301,114, now abandoned filed Jan. 25, 1989, which was a continuation-in-part of application Ser. No. 153,762, now abandoned filed Feb. 8, 1988. The entire disclosures of those applications are hereby incorporated by reference.

FIELD OF THE INVENTION

This invention relates to new polymer systems for topical ophthalmic application and to their preparation. More particularly, this invention relates to new topical ophthalmic delivery systems for controlled, sustained release of medicaments after administration in reliable drop form at a suitable initial viscosity which then substantially increases upon contact with the tear fluid.

BACKGROUND OF THE INVENTION

In topical administration of medicaments to the eye, a variety of factors can be important, among them comfort, consistency and accuracy of dosage, type and time of any vision interference, ease of administration, and timing of delivery. Prior ophthalmic delivery vehicles have suffered drawbacks in one or more of those areas.

For example, eyedrops in the form of aqueous solutions or suspensions are rapidly washed away by the eye's tear fluid. Ointments or creams blur the vision, and also have comparatively short residence times in the eye. Gelatin lamellae or other films or sheets, ocular inserts and non-aqueous suspensions and emulsions all can cause immediate pain and continuing discomfort and can also interfere with vision.

Highly viscous aqueous gels formed from carboxy vinyl polymers, such as those disclosed in Schoenwald et al. U.S. Pat. Nos. 4,271,143 and 4,407,792, issued June 2, 1981 and Oct. 4, 1983, respectively, are difficult to administer so as to provide consistent, accurate dosages and may be uncomfortable to administer as well. Indeed, above a viscosity of about 30,000 cps, reliable administration in drop form is at best difficult to achieve and at worst impossible. However, at viscosities low enough for reliable administration in drop form, such low viscosities impose an undesirable limitation on delivery efficiency because they render the suspension more amenable to dilution by tears Of course, higher viscosity suspensions may be employed in an effort to get the suspensions to remain in the eye for a prolonged time period, but such higher viscosities impair ease of administration of accurate drop dosages.

UK Patent Application No. GB 2007091A (Toko) describes carboxy vinyl polymer based gels over a wider viscosity range, namely 1,000 to 100,000 cps. The relatively low viscosity preparations having viscosities of 1,000 to 10,000 are stated to have good flowability and to be amenable to application by drops directly into the mucous membrane around the eyeball. The preparations having viscosities of from 10,000 to 100,000 cps are stated to be amenable to application to the eyelids like conventional ointments. However, in both higher and lower viscosity situations it is stated that the tears liquify the gel. The use of sodium chloride in the preparation is recommended in Toko for sustained efficiency because sodium chloride is said to delay breakdown of the gel when the compositions are applied to the mucous membrane of the eye. However, the sodium chloride is also said to convert the gel to a liquid with a great reduction in viscosity. Therefore, when sodium chloride is added to the composition, increased polymer amounts are recommended to compensate for such viscosity reduction due to the addition of sodium chloride.

Although delaying breakdown of a gel of a given viscosity by using the Toko teachings might have some benefits, it is that given viscosity which will influence whether reliable administration in drop form is achievable or whether ointment-like administration, together with its dosage problems, will be dictated. Whether the alleged sustained efficiency benefit said in Toko to be associated with a sodium chloride additive could even be accomplished at viscosities suitable for drop administration is far from clear from Toko. Nevertheless, even if such a benefit could be obtained with a Toko formulation at a viscosity for administration by drops, the fact that the starting viscosity is at a level low enough to even permit administration by drops is itself limiting on the so-called sustained efficiency. Indeed, as stated in the Toko document, when the preparations are applied, the tears liquify the gel. The sodium chloride merely is said to delay that breakdown.

It would, therefore, be desirable to provide an ophthalmic delivery system which is administrable at a viscosity suitable for reliable drop dosages, but which substantially increases in viscosity after administration. In that way, the drawbacks of either higher or lower viscosity need not be accepted in order to obtain the benefit of the other.

Robinson, U.S. Pat. No. 4,615,697, issued Oct. 7, 1986, discloses a controlled release treatment based on a bioadhesive which is described as a water-swellable, although water insoluble, fibrous, cross-linked carboxyfunctional polymer with a plurality of repeating units in which about at least 80 percent thereof contain at least one carboxy functionality and a crosslinking agent (0.05 to 1.5 percent) that is substantially free of polyalkenyl polyether. It is, first of all, noteworthy that whereas Robinson seeks to exclude the use of polyalkenyl polyether crosslinkers (as are present in Carbapol 934), Toko finds Carbapol 934 especially useful. Moreover, quite apart from that, Robinson neither discloses nor suggests a suspension that is administrable in drop form at a suitable viscosity and which undergoes rapid gelation upon contact with the tears.

OBJECTS AND SUMMARY OF THE INVENTION

It is an object of this invention to provide new topical ophthalmic medicament delivery methods and systems (and methods of their preparation) which overcome or minimize problems of the sort previously noted.

It is also an object of this invention to provide new topical ophthalmic medicament delivery methods and systems that are easily administrable to the eye in drop form.

A further object of this invention is to provide such new topical ophthalmic medicament delivery methods and systems which employ aqueous suspensions of particular lightly crosslinked polymers of acrylic acid or the like containing an ophthalmic medicament.

Yet another object of this invention is to provide new topical ophthalmic medicament delivery systems that are easily administrable in drop form and, after coming into contact with the eye's tear fluid, rapidly gel in the eye to a substantially greater viscosity than the viscosity of the administered drop.

A still further object of this invention is to provide methods of preparing these new topical ophthalmic medicament delivery systems.

In accordance with a preferred form of the invention intended to accomplish at least some of the foregoing objects, a sustained release topical ophthalmic medicament delivery system comprises an aqueous suspension at a pH of from about 3 to about 6.5 and an osmotic pressure of from about 10 to about 400 mOsM containing from about 0.1% to about 6.5% by weight, based on the total weight of the suspension, of a carboxyl-containing polymer prepared by polymerizing one or more carboxyl-containing monoethylenically unsaturated monomers and less than about 5% by weight of a crosslinking agent, such weight percentages of monomers being based on the total weight of monomers polymerized. The suspension has an initial viscosity of from about 1,000 to about 30,000 centipoises and is administrable to the eye in drop form at that initial viscosity. The polymer has average particle size of not more than about 50 μm, preferably not more than about 30 μm, in equivalent spherical diameter. It is lightly cross-linked to a degree such that although the suspension is administrable in drop form, upon contact of the lower pH suspension with the higher pH tear fluid of the eye, the suspension is rapidly gellable to a substantially greater viscosity than the viscosity of the suspension as originally administered in drop form. Accordingly, the resulting more viscous gel can remain in the eye for a prolonged period of time so as to release a medicament contained therein in sustained fashion.

The polymer is preferably prepared from at least about 50% by weight, more preferably at least about 90% by weight, of one or more carboxyl-containing monoethylenically unsaturated monomers. Desirably the polymer is prepared by suspension or emulsion polymerizing acrylic acid and a non-polyalkenyl polyether difunctional crosslinking agent to a particle size of not more than about 50 μm, preferably not more than about 30 μm, in equivalent spherical diameter. A preferred crosslinking agent is divinyl glycol. It may be desirable to replace up to about 40% by weight of the carboxyl-containing monoethylenically unsaturated monomers by one or more non-carboxyl-containing monoethylenically unsaturated monomers containing only physiologically and ophthamologically innocuous substituents.

The osmotic pressure is preferably achieved by using a physiologically and ophthalmologically acceptable salt in an amount of from about 0.01% to about 1% by weight, based on the total weight of the suspensions. A preferred salt is sodium chloride.

Medicament may be present in desired amount, preferably 0.005% to about 10% by weight, based on the total weight of the suspension. Preferred medicaments include fluorometholone and pilocarpine.

In a preferred method of preparing sustained release topical ophthalmic delivery systems, the foregoing suspensions are prepared and packaged at the desired viscosity of from 1,000 to about 30,000 centipoises, for administration to the eye in drop form. In a preferred delivery method, the foregoing suspensions, containing the medicament, are administered to the eye at the initial viscosity in drop form to cause the administered suspension, upon contact with the higher pH tear fluid of the eye, to rapidly gel in situ to a substantially greater viscosity than the viscosity of the suspension as originally administered in drop form. The more viscous gel remains in the eye for a prolonged period of time so as to release the medicament, entrapped in the more viscous gel formed in the eye, in sustained fashion.

In contrast to other systems, the present invention provides an ophthalmic delivery system that not only has the benefits of administration in drop form, but also does not suffer from breakdown limitations due to administration at a viscosity suitable for drops. Through administration at a viscosity such that the suspension can be reliably administered in drop form, but which actually increases when the suspension is so administered, controlled release of medicament is significantly enhanced.

As mentioned above, viscosities substantially over 30,000 cps are not suitable for drops. When the viscosities are substantially lower than 1,000 cps, the ability to gel upon contact with tears is impeded. The increased gelation upon contact with the tears occurs with a pH change when the suspension at a pH of from about 3 to about 6.5 and an osmotic pressure of from about 10 to about 400 mOsM contacts the tear fluid. As will be appreciated, tear fluid is at a higher pH of about 7.2 to about 7.4. With the pH increase, carboxylic acid (COOH) undergoes a sodium replacement (to COONa), and the sodium form disassociates, causing the polymer to expand.

This is where relationships of crosslinking and particle size become quite significant. Because the particles are present in a suspension, the degree of crosslinking is necessarily at a level such as to have avoided substantial dissolution of the polymer. On the other hand, since rapid gelation is achieved at the time of the pH change, the degree of crosslinking is necessarily not so great that gelation is precluded. Moreover, if the polymer particle size is too large, induced swelling can tend to take up voids in the volume between large particles that are in contact with one another, rather than the swelling tending to cause gelation.

If the polymer were in a dissolved state, as it would be if there were insufficient crosslinking because of a too low of a ratio of crosslinker to monomer, particle size would be basically irrelevant. In a suspension, particle size can be relevant to comfort. However, it has been found that in the system of the present invention, the small particle size and light crosslinking synergistically yield rapid gelation to a substantially increased viscosity when the pH changes. In fact, above the 50 μm size this advantage of substantially increased viscosity is not realized. Moreover, at the 50 μm size, there is also reasonably good eye comfort.

Although there has been prior disclosure that small particles are desirable to avoid vision impairment (Robinson, supra, col. 10, lines 16-20), that disclosure has not taught particle size limits contemplated for the present invention, especially not for realization of the in situ gelation benefits achievable by such sizes with appropriate light crosslinking in a system where viscosity is at an initial level suitable for drop administration, but which substantially increases upon tear contact.

In the most preferred forms of the invention, the particles are not only subject to the upper size limits described above, but also to a narrow particle size distribution. Such use of a monodispersion of particles, which aids in good particle packing, yields a maximum increased viscosity upon contact of the suspension with the tears and increases eye residence time. At least about 80%, more preferably at least about 90% and most preferably at least about 95%, of the particles should be within a no more than about 10 μm band of major particle size distribution, and overall (i.e., considering particles both within and outside such band) there should be no more than about 20%, preferably no more than about 10% and most preferably no more than about 5% fines (i.e., particles of a size below 1 μm. It is also preferred that as the average particle size is lowered from the upper limit of 50 μm, more preferably 30 μm, to lower sizes such as 6 μm, that the band of major particle size distribution be also narrowed, for example to 5 μm. Preferred sizes for particles within the band of major particle distribution are less than about 30 μm, more preferably less than about 20 μm, most preferably from about 1 μm to about 5 μm.

The foregoing and other aspects, objects and advantages of the present invention, as well as its nature, scope and utilization, will become more apparent to those skilled in the art from the following detailed description and the appended claims.

DETAILED DESCRIPTION OF THE INVENTION

The lightly crosslinked polymers of acrylic acid or the like used in practicing this invention are, in general, well known in the art. In a preferred embodiment such polymers are ones prepared from at least about 90% and preferably from about 95% to about 99.9% by weight, based on the total weight of monomers present, of one or more carboxyl-containing monoethylenically unsaturated monomers. Acrylic acid is the preferred carboxyl-containing monoethylenically unsaturated monomer, but other unsaturated, polymerizable carboxyl-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like can be used in addition to or instead of acrylic acid.

Such polymers are crosslinked by using a small percentage, i.e., less than about 5%, such as from about 0.5% or from about 0.1% to about 5%, and preferably from about 0.2% to about 1%, based on the total weight of monomers present, of a polyfunctional crosslinking agent. Included among such crosslinking agents are non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallylmethacrylamide and the like. Also included are polyalkenyl polyether crosslinking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053. Diolefinic non-hydrophilic macromeric crosslinking agents having molecular weights of from about 400 to about 8,000, such as insoluble di- and polyacrylates and methacrylates of diols and polyols, diisocyanate-hydroxyalxyl acrylate or methacrylate reaction products, and reaction products of isocyanate terminated prepolymers derived from polyester diols, polyether diols or polysiloxane diols with hydroxyalkylmethacrylates, and the like, can also be used as the crosslinking agents; see, e.g., Mueller et al. U.S. Pat. Nos. 4,192,827 and 4,136,250.

The lightly crosslinked polymers can of course be made from a carboxyl-containing monomer or monomers as the sole monoethylenically unsaturated monomer present, together with a crosslinking agent or agents. They can also be polymers in which up to about 40%, and preferably from about 0% to about 20% by weight, of the carboxyl-containing monoethylenically unsaturated monomer or monomers has been replaced by one or more non-carboxyl-containing monoethylenically unsaturated monomers containing only physiologically and ophthalmologically innocuous substituents, including acrylic and methacrylic acid esters such as methyl methacrylate, ethyl acrylate, butyl acrylate, 2-ethylhexylacrylate, octyl methacrylate, 2-hydroxyethyl-methacrylate, 3-hydroxypropylacrylate, and the like, vinyl acetate, N-vinylpyrrolidone, and the like; see Mueller et al. U.S. Pat. No. 4,548,990 for a more extensive listing of such additional monoethylenically unsaturated monomers. Particularly preferred polymers are lightly crosslinked acrylic acid polymers wherein the crosslinking monomer is 2,3-dihydroxyhexa-1,5-diene or 2,3-dimethylhexa-1,5-diene.

The lightly crosslinked polymers used in practicing this invention are preferably prepared by suspension or emulsion polymerizing the monomers, using conventional free radical polymerization catalysts, to a dry particle size of not more than about 50 μm in equivalent spherical diameter; e.g., to provide dry polymer particles ranging in size from about 1 to about 30 μm, and preferably from about 3 to about 20 μm, in equivalent spherical diameter. In general, such polymers will range in molecular weight estimated to be about 250,000 to about 4,000,000, and preferably about 500,000 to about 2,000,000.

Aqueous suspensions containing polymer particles prepared by suspension or emulsion polymerization whose average dry particle size is appreciably larger than about 50 μm in equivalent spherical diameter are less comfortable when administered to the eye than suspensions otherwise identical in composition containing polymer particles whose equivalent spherical diameters are, on the average, below about 50 μm. Moreover, above the average 50 μm size, the advantage of substantially increased viscosity after administration is not realized. It has also been discovered that lightly crosslinked polymers of acrylic acid or the like prepared to a dry particle size appreciably larger than about 50 μm in equivalent spherical diameter and then reduced in size, e.g., by mechanically milling or grinding, to a dry particle size of not more than about 50 μm in equivalent spherical diameter do not work as well as polymers made from aqueous suspensions. While we do not wish to be bound by any theory or mechanism advanced to explain the functioning of this invention, one possible explanation for the difference of such mechanically milled or ground polymer particles as the sole particulate polymer present is that grinding disrupts the spatial geometry or configuration of the larger than 50 μm lightly cross-linked polymer particles, perhaps by removing uncross-linked branches from polymer chains, by producing particles having sharp edges or protrusions, or by producing ordinarily too broad a range of particle sizes to afford satisfactory delivery system performance. A broad distribution of particle sizes will impair the viscosity-gelation relationship. In any event, such mechanically reduced particles are less easily hydratable in aqueous suspension than particles prepared to the appropriate size by suspension or emulsion polymerization, and also are less able to gel in the eye under the influence of tear fluid to a sufficient extent and are less comfortable once gelled than gels produced in the eye using the aqueous suspensions of this invention. However, up to about, 40% by weight, e.g., from about 0% to over 20% by weight, based on the total weight of lightly crosslinked particles present, of such milled or ground polymer particles can be admixed with solution or emulsion polymerized polymer particles having dry particle diameters of not more than about 50 μm when practicing this invention. Such mixtures will also provide satisfactory viscosity levels in the ophthalmic medicament delivery systems and in the in situ gels formed in the eye coupled with ease and comfort of administration and satisfactory sustained release of the medicament to the eye, particularly when such milled or ground polymer particles, in dry form, average from about 0.01 to about 30 μm, and preferably from about 1 to about 5 μm, in equivalent spherical diameter.

In the most preferred embodiment of the invention, the particles have a narrow particle size distribution within a 10 μm band of major particle size distribution which contains at least 80%, more preferably at least 90%, most preferably at least 95% of the particles. Also, there is no more than 20%, preferably no more than 10%, and most preferably no more than 5% particles of a size below 1 μm. The presence of large amounts of such fines has been found to inhibit the desired gelation upon eye contact. Apart from that, the use of a monodispersion of particles will give maximum viscosity and an increased eye residence time of the ophthalmic medicament delivery systems for a given particle size. Monodisperse particles having a particle size of 30 μm and below are most preferred. Good particle packing is aided by a narrow particle size distribution.

The aqueous suspensions of this invention will contain amounts of lightly crosslinked polymer particles ranging from about 0.1% to about 6.5% by weight, and preferably from about 0.5% to about 4.5% by weight, based on the total weight of the aqueous suspension. They will preferably be prepared using pure, sterile water, preferably deionized or distilled, having no physiologically or ophthalmologically harmful constituents, and will be adjusted to a pH of from about 3.0 to about 6.5, and preferably from about 4.0 to about 6.0, using any physiologically and ophthalmologically acceptable pH adjusting acids, bases or buffers, e.g., acids such as acetic, boric, citric, lactic, phosphoric, hydrochloric, or the like, bases such as sodium hydroxide, sodium phosphate, sodium borate, sodium citrate, sodium acetate, sodium lactate, THAM (trishydroxymethylaminomethane), or the like and salts and buffers such as citrate/dextrose, sodium bicarbonate, ammonium chloride and mixtures of the aforementioned acids and bases.

When formulating the aqueous suspensions of this invention, their osmotic pressure ($\pi$) will be adjusted to from about 10 milliosmolar (mOsM) to about 400 mOsM, and preferably from about 100 to about 250 mOsM, using appropriate amounts of physiologically and ophthalmologically acceptable salts. Sodium chloride is preferred to approximate physiologic fluid, and amounts of sodium chloride ranging from about 0.01% to about 1% by weight, and preferably from about 0.05% to about 0.45% by weight, based on the total weight of the aqueous suspension, will give osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfite and the like, e.g., potassium chloride, sodium thiosulfate, sodium bisulfite, ammonium sulfate, and the like can also be used in addition to or instead of sodium chloride to achieve osmolalities within the above-stated ranges.

The amounts of lightly crosslinked polymer particles, the pH, and the osmotic pressure chosen from within the above-stated ranges will be correlated with each other and with the degree of crosslinking to give aqueous suspensions having viscosities ranging from about 1,000 to about 30,000 centipoise, and preferably from about 5,000 to about 20,000 centipoise, as measured at room temperature (about 25° C.) using a Brookfield Digital LVT Viscometer equipped with a number 25 spindle and a 13R small sample adapter at 12 rpm. The correlations of those parameters are also such that the suspensions will gel on contact with tear fluid to give gels having viscosities estimated to range from about 75,000 to about 500,000 centipoise, e.g., from about 200,000 to about 300,000 centipoise, measured as above, depending on pH as observed, for example, from pH-viscosity curves. This effect is noted by observing a more viscous drop on the eye as a set cast. The cast, after setting, can be easily removed.

The viscous gels that result from fluid eyedrops delivered by means of the aqueous suspensions of this invention have residence times in the eye ranging from about 2 to about 12 hours, e.g., from about 3 to about 6 hours. The medicaments contained in these drug delivery systems will be released from the gels at rates that depend on such factors as the drug itself and its physical form, the extent of drug loading and the pH of the system, as well as on any drug delivery adjuvants, such as ion exchange resins compatible with the ocular surface, which may also be present. For fluorometholone, for example, release rates in the rabbit eye in excess of four hours, as measured by fluorometholone contained in the aqueous humor, have been observed.

Medicaments—substances used in treating or ameliorating a disease or medical condition—including drugs intended to treat therapeutically the eye itself or the tissues surrounding the eye and drug administered via the ophthalmic route to treat therapeutically a local condition other than one involving the eye, will typically be incorporated in the topical delivery systems of this invention in therapeutically active amounts comparable to amounts administered in other dosage forms, usually in amounts ranging from about 0.005% to about 10% by weight, and preferably from about 0.01% to about 5% by weight, based on the total weight of the formulation. Thus, for example, from about 0.01% to about 1% by weight of the anti-inflammatory steroid fluorometholone can be administered in this manner.

An illustrative but by no means exhaustive listing of such medicaments includes demulcents (for relief of "dry eye"), antibiotics, antivirals, steroids, aminosubstituted steroids, including anti-inflammatory agents, peptides, polypeptides, cardiotonics, antihypertensives, antiallergics, alpha- and betaadrenergic blocking agents, ophthalmic medicaments such as anticataract agents, antiglaucoma agents and ophthalmic antiinflammatory agents, ophthalmic lubricating agents, ophthalmic topical or regional anesthetic agents, etc. Specific medicaments that can be used in the present invention include drugs such as pilocarpine, idoxuridine, carbachol, bethanechol, timolol, atenolol, labetolol, metoprolol, nadolol, oxprenolol, pindolol, sotalol, betaxolol, acebutolol, alprenolol, levo-bunolol, p-aminoclonidine, dipivefrin, tetracycline, epinephrine, phenylephrine, eserine, phospholine, aceclidine, demecarium, cyclopentolate, homatropine, scopolamine, nitroglycerin, ethacrynic acid, furosemide, amiloride, chlortetracycline, bacitracin, neomycin, polymyxin, polymyxin B, gramicidin, oxytetracycline, chloramphenicol, gentamycin, penicillins, erythromycin, sulfacetamide, tobramycin, trospectomycin, vancomycin, ciprofloxacin, perfloxacin, olfloxacin, enoxacin, naphazoline hydrochloride, clindamycin, isofluorophate, fluorometholone, dexamethasone, hydrocortisone, fluorocinolone, medrysone, prednisolone, prednisolone acetate, methylprednisolone, fluticasone propionate, betamethasone, triamcinolone, estradiol, ibuprofen, flurbiprofen, naproxen, esters of ibuprofen, flurbiprofen, and naproxen; ketorolac, suprofen, interferons, cromolyn, gancyclovir, aminozolamide, alltrans-retinoic acid (Vitamin A) and the nontoxic, pharmaceutically acceptable salts thereof. Pro-drug counterparts are also within the scope of the present invention. Ophthalmic lubricating agents are materials capable of inducing natural lacrimation or creating artificial lacrimation and include, for example, polyvinylalcohol, cellulose polymers such as hydroxypropyl methyl cellulose, polylactams such as polyvinylpyrrolidone and the like. "Dry eye" formulations that comprise pure water and a lightly crosslinked polymer of the type described hereinabove in an amount within the range also set forth hereinabove, hypotonic in saline and thus having the requisite osmotic pressure but at a pH in the range of about 3 to about 6.5, are also contemplated as being within the scope of this invention. Topical or regional anesthetic agents include ones used during ophthalmic surgery or other ophthalmic procedures, such as lidocaine, cocaine, benoxinate, dibucaine, proparacaine, tetracaine, etidocaine, procaine, hexylcaine, bupivacaine, mepivacaine, prilocaine, chloroprocaine, and the like.

The term "pharmaceutically acceptable salt" refers to those salts of the parent compound that do not significantly or adversely affect the pharmaceutical properties (e.g., toxicity, efficacy, etc.) of the parent compound. Pharmaceutically acceptable salts administrable by means of the aqueous suspensions of this invention include, for example, chloride iodide, bromide, hydrochloride, acetate, nitrate, stearate, pamoate, phosphate and sulfate salts. It is sometimes desirable to use an appropriate salt form of the medicament that increases the water solubility or polar characteristics of the free drug.

The aqueous suspension topical ophthalmic medicament delivery systems of this invention can be formulated in any of several ways. For example the drug, the lightly crosslinked polymer particles, and the osmolality-adjusting salt can be preblended in dry form, added to all or part of the water, and stirred vigorously until apparent polymer dispersion is complete, as evidenced by the absence of visible polymer aggregates. Sufficient pH adjusting agent is then added incrementally to reach the desired pH, and more water to reach 100 percent formula weight can be added at this time, if necessary. Another convenient method involves adding the drug to about 95 percent of the final water volume and stirring for a sufficient time to saturate the solution. Solution saturation can be determined in known manner, e.g., using a spectrophotometer. The lightly crosslinked polymer particles and the osmolality-adjusting salt are first blended in dry form and then added to the drug—saturated suspension and stirred until apparent polymer hydration is complete. Following the incremental addition of sufficient pH adjusting agent to reach the desired pH, the remainder of the water is added, with stirring, to bring the suspension to 100 percent formula weight.

These aqueous suspensions can be packaged in preservative-free, single-dose non-reclosable containers. This permits a single dose of the medicament to be delivered to the eye one drop at a time, with the container then being discarded after use. Such containers eliminate the potential for preservative-related irritation and sensitization of the corneal epithelium, as has been observed to occur particularly from ophthalmic medicaments containing mercurial preservatives. Multiple-dose containers can also be used, if desired, particularly since the relatively low viscosities of the aqueous suspensions of this invention permit constant, accurate dosages to be administered dropwise to the eye as many times each day as necessary. In those suspensions where preservatives are to be included, suitable preservatives are chlorobutanol, Polyquat, benzalkonium chloride, cetyl bromide, and the like.

In order that those skilled in the art can more fully appreciate aspects of this invention, the following examples are set forth. These examples are given solely for purposes of illustration, and should not be considered as expressing limitations unless so set forth in the appended claims.

EXAMPLE I

A pre-blend was prepared by dry-blending together 0.10 weight percent of fluorometholone ($11\beta$, $17\alpha$-dihydroxy-$9\alpha$-fluoro-$6\alpha$-methylpregna-1, 4-diene-3,20-dione), 1 25 weight percent of Carbopol 976 (formerly known as Carbopol EX 55) (a carboxylcontaining polymer prepared by suspension polymerizing acrylic acid and divinyl glycol; The B. F. Goodrich Company) having a particle size of 5 $\mu$m, and 0.15 weight percent of sodium chloride. This pre-blend was added to 80 weight percent of deionized water in a vessel and stirred at 20 rpm at about 25° C. for 12 hours. At this point apparent polymer dispersion was complete as evidenced by the absence of visible polymer aggregates.

The resulting aqueous drug-containing suspension was then titrated with lON aqueous sodium hydroxide to pH 4.53; following which additional deionized water was added, with stirring, to bring the final formulation weight to 100 percent. The final aqueous suspension had an osmolality of approximately 50 mOsM and a viscosity of approximately 12,000 centipoise as measured at 25° C. on a Brookfield Digital LVT Viscometer equipped with a number 25 spindle and a 13R small sample adapter at 12 rpm.

EXAMPLE II

Fluorometholone, 0.10 weight percent, was added to 80 weight percent of deionized water in a vessel and stirred at 50 rpm at 25° C. for 24 hours to give a saturated aqueous suspension of the drug. Carbopol 976 polymer having a 5 $\mu$m particle size, 1.40 weight percent, and 0.25 weight percent of sodium chloride were blended in dry form and this blend was then added to the drug-saturated suspension, with stirring, at 20 rpm at 25° C. for 12 hours.

The resulting aqueous drug-containing suspension was then titrated with 10N aqueous sodium hydroxide to pH 4.49, following which additional deionized water was stirred into the suspension to bring the final formulation weight to 100 percent. The final aqueous suspension had an osmolality of approximately 90 mOsM and a viscosity of approximately 18,000 centipoise, measured as in Example I.

EXAMPLES III–VIII

These examples relate to the preparation or "dry eye" formulations (Examples III–V) and pilocarpine hydrochloride formulations (Examples VI–VIII) of the present invention. For each example, NaCl and Carbopol 976, in the indicated weights, were dissolved in 100 g of distilled water using a mechanical mixer, after which the resulting formulation was sterilized at 121° C. for 30 to 45 minutes. NaOH was then sterile-filtered to adjust the pH to the indicated range. In the pilocarpine examples, the pilocarpine hydrochloride was added by sterile filtration and the pH was adjusted following the sterilization. Carbopol 976 in all examples had a particle size of 5 $\mu$m.

| | Dry Eye Formulations | | |
|---|---|---|---|
| No. | Carbopol 976 (w/w %) | NaCl (w/w %) | pH |
| III | 1.05 | 0.175 | 5.6–5.8 |
| IV | 1.05 | 0.050 | 5.6–5.8 |
| V | 0.80 | 0.600 | 5.6–5.8 |

| | Pilocarpine Hydrochloride Formulations | | | |
|---|---|---|---|---|
| No. | Pilocarpine (w/w %) | Carbopol 976 (w/w %) | NaCl (w/w %) | pH |
| VI | 1.0 | 2.0 | 0.1–0.9 | 5.2–5.8 |
| VII | 2.0 | 2.0 | 0.1–0.9 | 5.2–5.8 |
| VIII | 4.0 | 2.0 | 0.1–0.9 | 5.2–5.8 |

EXAMPLE IX

Various formulations were compounded to establish that the viscosity of the polymer solution is dependent on particle size. There were used Carbopol 976 and polycarbophil, another polymer within the scope of the present invention. Polycarbophil, as referred to here, is a polyacrylic-acid polymer lightly cross-linked with divinyl glycol, meeting the compendium specifications of the United States Pharmacopeia, and was obtained as an experimental sample from The B. F. Goodrich Company.

A polycarbophil lot was sieved to ranges of greater than 105 $\mu$m, less than 105 $\mu$m, less than 105 but greater than 75 $\mu$m, and less than 75 but greater than 45 $\mu$m. A sample was also ground to a size of less than 10 $\mu$m.

The general formulation used for all was 1.05 w/w% polymer and 0.2 w/w% NaCl with a pH of 5.2–5.6. The correlation between particle size and viscosity is shown in the following table.

| Polymer | Viscosity (cps)* | (Dry) Nominal Particle Size ($\mu$m) |
|---|---|---|
| Carbopol 976 | 28,000 | 5 |
| Polycarbophil | 1,080 | <105 |
| Polycarbophil | 19,800 | <10 |
| Polycarbophil | 1,800 | >105 |
| Polycarbophil | 2,800 | >75 and <105 |
| Polycarbophil | 9,200 | >45 and <75 |
| 80 parts Carbopol 976/ 20 parts Polycarbophil | 19,200 | 5/<105 |
| 90 parts Carbopol 976/ 10 parts Polycarbophil | 22,000 | 5/<105 |

*Measured at about 25° C. using a Brookfield Digital LVT Viscometer equipped with a number 25 spindle and a 13R small sample adapter at 12 rpm.

EXAMPLE X

This example is directed to a fluorometholone suspension within the scope of the present invention.

Fluorometholone, 0.10 weight %, was added to 97 weight % of purified water in a vessel and stirred at high speed for 15 minutes to give a finely dispersed aqueous suspension of the drug. Carbopol 976 polymer having a dry particle size of 5 $\mu$m, 1.05 weight %, was added to the drug suspension with stirring and mixing was continued for a minimum of 15 minutes. After the 15-minute minimum time had elapsed, 0.20 weight % of sodium chloride was added.

The resulting aqueous drug-containing suspension was sterilized at 121° C. for 45 minutes. The suspension was cooled to about 50° C. and a 10 N sodium hydroxide solution was then sterile filtered into the suspension with stirring to adjust the pH to 5.6–5.8. Additional purified water was sterile filtered into the suspension with stirring to bring the final formulation weight to 100%. The final aqueous suspension had an osmolality of approximately 150 mOsM, a viscosity of approximately 15,700 centipoise, measured at room temperature (about 25° C.) using a Brookfield Digital LVT Viscometer equipped with a number 25 spindle and a 13R small sample adapter at 12 RPM, and a pH of about 5.6–5.8.

EXAMPLE XI

Polycarbophil is prepared by suspension polymerizing acrylic acid lightly cross-linked with divinyl glycol. The lot is sieved to sublots such as those in ranges of less than 50 $\mu$m, between 40 $\mu$m and 50 $\mu$m, between 30 $\mu$m and 40 $\mu$m, less than 30 $\mu$m, between 20 $\mu$m and 30 $\mu$m, between 10 $\mu$m and 20 $\mu$m, between 5 $\mu$m and 15 $\mu$m, and less than 5 $\mu$m. All of the sublots are sieved to remove the fines, i.e., particles of less than 1 $\mu$m. Various monodispersions are then prepared as blends from the sublots. Each of the monodispersions has a major particle size distribution of at least about 80%, more preferably at least about 90%, and most preferably at least about 95%, within a no more than 10 $\mu$m band. Of the particles within and outside that band, no more of the total than about 20%, preferably no more than about 10%, and most preferably no more than about 5% are fines. Preferred sizes for particles within the band of major particle distribution are less than about 30 $\mu$m, more preferably less than about 20 $\mu$m, and most preferably from about 1 $\mu$m to about 5 $\mu$m.

The monodisperse blends are added to the desired weight percent of deionized water in a vessel and stirred at 20 rpm at about 25° C. for about 12 hours or until apparent polymer dispersion is complete as evidenced by the absence of visible polymer aggregates.

The suspension is then titrated with 10N aqueous sodium hydroxide to a desired pH in the range of from about 3 to about 6.5. Sodium chloride is added to adjust the desired osmotic pressure to from about 10 mOsM to about 400 mOsM. The suspension contains from about 0.1% to about 6.5% by weight, based on the total weight of the suspension, of polycarbophil prepared by suspension polymerization of the acrylic acid and from about 0.1% to about 5% by weight of the divinyl crosslinking agent.

The amounts of lightly crosslinked polymer particles, the pH, the osmotic pressure, and the degree of crosslinking are correlated to yield aqueous suspensions having initial viscosities in the range of from about 1,000 to about 30,000 cps, more preferably from about 5,000 to about 30,000 cps, as measured at room temperature (about 25° C.) using a Brookfield Digital LVT Viscometer. The correlation of these parameters is also such that upon administration in drop form, the suspensions gel on contact with the tear fluid to substantially greater viscosities, preferably in the range of about 75,000 cps to about 500,000 cps, e.g., from about 200,000 cps to about 300,000 cps.

After such administration, the viscous gel remains in the eye for a prolonged period of time and is able to release a medicament contained therein in sustained fashion. In this connection, medicaments such as fluorometholone, pilocarpine or demulcents, in an amount of from about 0.005% to about 10% by weight based on the total weight of the suspension, are added during or after initial formulation.

The above discussion of this invention is directed primarily to preferred embodiments and practices thereof. It will be readily apparent to those skilled in the art that further changes and modifications in actual implementation of the concepts described herein can easily be made without departing from the spirit a-d scope of the invention as defined by the following claims.

We claim:

1. A sustained release topical ophthalmic medicament delivery system, comprising:
    an aqueous suspension at a pH of from about 3 to about 6.5 and an osmotic pressure of from about 10 to about 400 mOsM containing from about 0.1% to about 6.5% by weight, based on the total weight of the suspension, of a carboxyl-containing polymer prepared by polymerizing one or more carboxyl-containing monoethylenically unsaturated monomers and less than about 5% by weight of a cross-linking agent, such weight percentages of monomers being based on the total weight of monomers polymerized,
    said suspension having a viscosity of from about 1,000 to about 30,000 centipoises and being administrable to the eye in drop form,
    said polymer having average particle size of not more than about 50 μm in equivalent spherical diameter and being lightly cross-linked such that although the suspension is administrable in drop form, upon contact of the lower pH suspension with the higher pH tear fluid of the eye, the suspension is rapidly gellable to a substantially greater viscosity than the viscosity of the suspension as originally administered in drop form,
    whereby the resulting more viscous gel can remain in the eye for sustained release of a medicament contained therein.

2. A topical medicament delivery system as in claim 1 in which said polymer is one prepared from at least 50% weight of one or more carboxyl-containing monoethylenically unsaturated monomers.

3. A topical ophthalmic medicament delivery system as in claim 1 containing an ophthalmic medicament.

4. A topical ophthalmic medicament delivery system as in claim 3 in which said polymer has a particle size of not more than about 30 μm.

5. A topical ophthalmic medicament delivery system as in claim 1, claim 2 or claim 3 in which said polymer is a monodispersion of particles.

6. A topical ophthalmic medicament delivery system as in claim 5 wherein at least about 80% of the particles are within a no more than about 10 μm band of major particle size distribution and no more than about 20% of the total particles are fines.

7. The topical ophthalmic medicament delivery system as in claim 5 wherein at least about 90% of the particles are within a no more than about 10 μm band of major particle size distribution, and no more than about 10% of the total particles are fines.

8. The topical ophthalmic medicament delivery system as in claim 5 wherein at least about 95% of the particles are within a no more than about 10 μm band of major particle size distribution, and no more than about 5% of the total particles are fines.

9. The topical ophthalmic medicament delivery system as in claim 6 wherein the band of major particle distribution is from about 1 to about 5 μm.

10. The topical ophthalmic medicament delivery system as in claim 1 wherein the polymer is one in which up to about 40% by weight of said carboxyl-containing monoethylenically unsaturated monomers has been replaced by one or more non-carboxyl-containing monoethylenically unsaturated monomers.

11. A topical ophthalmic medicament delivery system as in claim 4 in which said polymer is one prepared from at least about 90% by weight of one or more carboxyl-containing monoethylenically un-saturated monomers.

12. A topical ophthalmic medicament delivery system as in claim 3 in which said polymer is one prepared by suspension or emulsion polymerizing acrylic acid and a non-polyalkenyl polyether difunctional crosslinking agent to a particle size of not more than about 50 μm in equivalent spherical diameter.

13. A topical ophthalmic medicament delivery system as in claim 12 in which said crosslinking agent is divinyl glycol.

14. A topical ophthalmic medicament delivery system as in claim 13 in which said osmotic pressure is achieved using a physiologically and ophthalmologically acceptable salt in an amount of from about 0.01% to about 1% by weight, based on the total weight of the suspension.

15. A topical ophthalmic medicament delivery system as in claim 14 in which said salt is sodium chloride.

16. A topical ophthalmic medicament delivery system as in claim 15 in which said medicament is present in an amount of from about 0.005% to about 10% by weight, based on the total weight of the suspension.

17. A topical ophthalmic medicament delivery system as in claim 16 in which said medicament is fluorometholone.

18. A topical ophthalmic medicament delivery system as in claim 16 in which said medicament is pilocarpine.

19. A method of delivering an ophthalmic medicament to the eye which comprises:

preparing an aqueous suspension at a pH of from about 3 to about 6.5 and an osmotic pressure of from about 10 to about 400 mOsM containing an ophthalmic medicament and from about 0.1% to about 6.5% by weight, based on the total weight of the suspension, of a carboxyl-containing polymer prepared by polymerizing one or more carboxyl-containing monoethylenically unsaturated monomers and from less than about 5% by weight of a cross-linking agent, such weight percentages of monomers being based on the total weight of monomers polymerized, said suspension having a viscosity of from about 1,000 to about 30,000 centipoises, and said polymer having an average particle size of not more than about 50 μm in equivalent spherical diameter and being lightly crosslinked, administering said suspension to the eye in drop form to cause the suspension, upon contact with the higher pH tear fluid of the eye, to rapidly gel to a substantially greater viscosity than the viscosity of the suspension as originally administered in drop form, whereby the resulting more viscous gel remains in the eye for sustained release of the medicament contained therein.

20. A method of claim 19 in which said polymer is one prepared from at least 50% weight of one or more carboxyl-containing monoethylenically unsaturated monomers.

21. A method as in claim 19 or claim 20 in which said polymer has a particle size of not more than about 30 μm.

22. A method as in claim 19 or claim 20 in which said polymer is one in which up to about 40% by weight of said carboxyl-containing monoethylenically unsaturated monomers has been replaced by one or more non-carboxyl-containing monoethylenically unsaturated monomers containing only physiologically and ophthalmologically innocuous substituents.

23. A method as in claim 19 in which said polymer is one prepared by suspension or emulsion polymerizing acrylic acid and a non-polyalkenyl polyether difunctional crosslinking agent to a particle size of not more than about 50 μm in equivalent spherical diameter.

24. A method as in claim 23 in which said cross-linking agent is divinyl glycol.

25. A method as in claim 24 in which said osmotic pressure is achieved using a physiologically and ophthalmologically acceptable salt in an amount of from about 0.01% to about 1% by weight, based on the total weight of the suspension.

26. A method as in claim 25 in which said salt is sodium chloride.

27. A method as in claim 26 in which said medicament is present in an amount of from about 0.005% to about 10% by weight, based on the total weight of the suspension.

28. A method as in claim 27 in which said medicament is fluorometholone.

29. A method as in claim 28 in which said medicament is pilocarpine.

30. A method as in claim 19, claim 20 or claim 21 in which said polymer is a monodispersion of particles.

31. A method as in claim 30 wherein at least about 80% of the particles are within a no more than about 10 μm band of major particle size distribution and no more than about 20% of the total particles are fines.

32. A method as in claim 30 wherein at least about 90% of the particles are within the 10 μm band of major particle size distribution, and no more than about 10% of the total particles are fines.

33. A method as in claim 30 wherein at least about 95% of the particles are within a no more than about 5 μm band of major particle size distribution and no more than about 20% of the total particles are fines.

34. A method as in claim 31 wherein the band of major particle distribution is from about 1 to about 5 μm.

35. A method of preparing a sustained release topical ophthalmic delivery systems, comprising: preparing an aqueous suspension at a pH of from about 3 to about 6.5 and an osmotic pressure of from about 10 to about 400 mOsM and containing from about 0.1% to about 6.5% by weight, based on the total weight of the suspension, of a carboxyl-containing polymer prepared by polymerizing one or more carboxyl-containing monoethylenically unsaturated monomers and less than about 5% by weight of a crosslinking agent, such weight percentages of monomers being based on the total weight of monomers polymerized, and packaging the suspension, at a viscosity of from 1,000 to about 30,000 centipoises, for administration to the eye in drop form, said polymer having average particle size of not more than about 50 μm in equivalent spherical diameter and being lightly cross-linked such that although the suspension is administrable in drop form, upon contact of the lower pH suspension with the higher pH tear fluid of the eye, the suspension is rapidly gellable to a substantially greater viscosity than the viscosity of the suspension as originally administered in drop form.

* * * * *